United States Patent [19]

Urquhart et al.

[11] Patent Number: 4,578,075
[45] Date of Patent: Mar. 25, 1986

[54] DELIVERY SYSTEM HOUSING A PLURALITY OF DELIVERY DEVICES

[75] Inventors: John Urquhart, Palo Alto; Felix Theeuwes, Los Altos, both of Calif.

[73] Assignee: ALZA Corporation, Palo Alto, Calif.

[21] Appl. No.: 451,329

[22] Filed: Dec. 20, 1982

[51] Int. Cl.[4] ............................................. A61M 7/00
[52] U.S. Cl. ...................................... 604/892; 424/19
[58] Field of Search .................. 604/890–897; 424/15–22, 32–35

[56] References Cited

U.S. PATENT DOCUMENTS

| | | | |
|---|---|---|---|
| 3,786,813 | 1/1974 | Michaels | 604/892 |
| 3,917,813 | 11/1975 | Pedersen | 424/20 |
| 4,193,985 | 3/1980 | Bechgaard et al. | 424/19 |
| 4,263,273 | 4/1981 | Appelgren et al. | 424/20 |
| 4,324,779 | 4/1982 | Dahlhausen et al. | 424/20 |
| 4,326,525 | 4/1982 | Swanson et al. | 604/892 |
| 4,339,428 | 7/1982 | Tencza | 424/21 |

FOREIGN PATENT DOCUMENTS 1204580 9/1970 United Kingdom .................. 424/37

Primary Examiner—C. Fred Rosenbaum
Assistant Examiner—Sherri E. Vinyard
Attorney, Agent, or Firm—Paul L. Sabatine; Edward L. Mandell; Steven F. Stone

[57] ABSTRACT

A delivery system is disclosed comprising a wall surrounding a lumen containing a plurality of osmotic delivery devices. The wall is formed of an environment sensitive material that releases the tiny osmotic devices into the environment. The osmotic devices comprise a semipermeable wall surrounding a compartment containing drug. A passageway through the semipermeable wall releases drug from the device to the environment.

2 Claims, 9 Drawing Figures

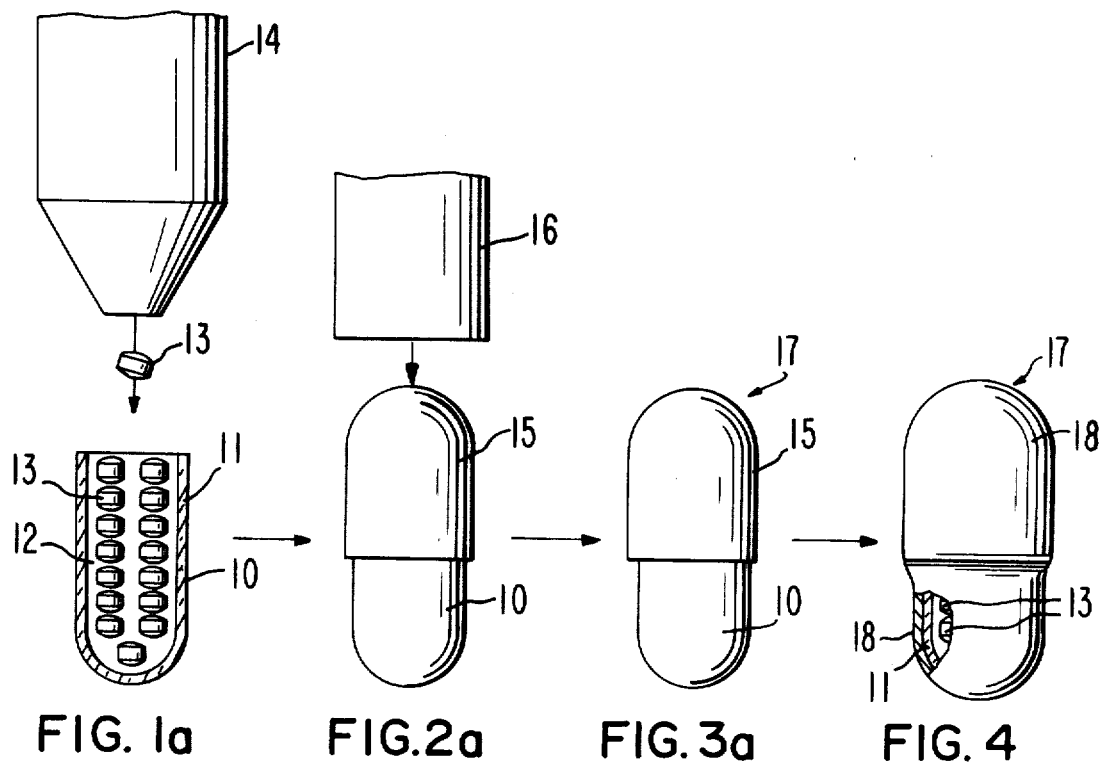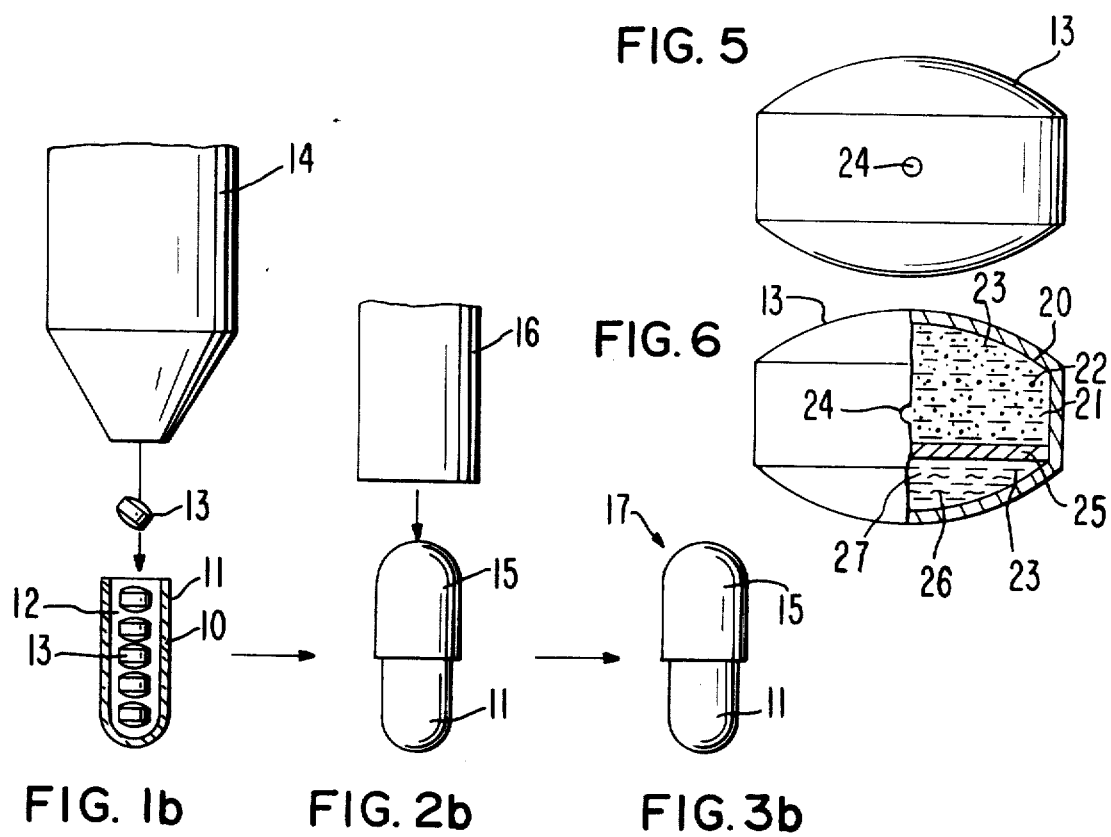

DELIVERY SYSTEM HOUSING A PLURALITY OF DELIVERY DEVICES

FIELD OF THE INVENTION

This invention pertains to both a novel and unique delivery system. More particularly, the invention relates to a delivery system comprising an exterior wall that surrounds a lumen housing a plurality of osmotic delivery devices. The exterior wall is formed of an environment sensitive material that releases the delivery devices into the environment. The delivery devices comprise a semipermeable wall that surrounds a compartment containing a drug with a passageway in the semipermeable wall for delivering the drug over time. The delivery system is useful for delivering a single drug, two drugs or more, that are separately housed and separately dispensed for (a) obtaining the therapeutic benefits of each drug, (b) lessening the incidence of adverse effects due to the incompatability of different drugs, or (c) delivering at least two drugs that are difficult to deliver from a dispensing system.

BACKGROUND OF THE INVENTION

Since the beginning of antiquity, both pharmacy and medicine have sought a delivery system for administering a beneficial drug. The first written reference to a dosage form is the Eber Papyrus, written about 1552 B.C. The Eber Papyrus mentions dosage forms such as anal suppositories, vaginal pessaries, ointments, oral pill formulations, and other dosage preparations. About 2500 years passed without any advance in dosage form development, when the Arab physician Rhazes, 865–925 A.D., invented the coated pill. About a century later the Persian Avicenna, 980–1037 A.D., coated pills with gold or silver for increasing patient acceptability and for enhancing the effectiveness of the drug. Also around this time, the first tablet was described in Arabian manuscripts written by al-Zahrawi, 936–1009 A.D. The manuscripts described a tablet formed from the hollow impressions in two facing tablet molds. Pharmacy and medicine waited about 800 years for the next innovation in dosage forms, when in 1883 Mothes invented the capsule for administering drug. The next quantum leap in dosage forms came in 1972 with the invention of the osmotic delivery device by inventors Theeuwes and Higuchi. The osmotic delivery device is manufactured in one embodiment for oral use, and in this embodiment it embraces the appearance of a tablet with a drug delivery portal. It is the first oral dosage form that delivers a given amount of drug per unit time at a controlled and known rate of delivery over a prolonged period of time.

Also, since the beginning of antiquity, pharmacy and medicine considered it desirable to prescribe pharmaceutical dosage forms containing at least two different drugs for obtaining the pharmacological benefits of each drug. The coadministration of certain drugs is prescribed often in fixed ratios for several reasons. For example, for drugs that have the same therapeutic effect but act mechanistically different on the body, such combinations may have the added therapeutic effect of both agents but less side effects, or the drugs may act synergistically and create a larger than additive effect. Also, drug combinations are prescribed for treatments where each individual drug addresse different symptoms of a particular medical situation. Although, a large number of therapeutic combinations could be provided, often they can not be compounded in the same dosage form because each drug needs to be administered on a different schedule. The different schedule is needed because each drug has a different biological half life and therapeutic index and therefore each drug should be administered in separate dosage forms on a prescribed schedule that is specific for each drug. Thus, a drug that needs to be administered four times a day, should not be combined with a drug that should be administered once a day. These drugs are kinetically incompatible in a pharmaceutical dosage form. Another reason why certain drugs cannot be combined is they may be chemically incompatible or unstable in the presence of each other. This kinetic or chemical incompatibility can be eliminated by the novel dosage form provided by this invention. For example, by using the dosage form provided by this invention, a regimen consisting of four times a day administration of drug can be transformed into a once a day administration such that the drug previously administered four times daily can be combined with a drug administered once daily. In other words, both drugs can be coadministered to the body at delivery rates that are matched to achieve each of their separate therapeutic plasma concentrations. Thus, in the light of the above presentation, it will be appreciated by those versed in the dispensing art, that if an improved delivery system is made available for housing a drug or two or more different drugs for independent or for simultaneous independent codelivery, at continuous and controlled rates in therapeutically effective amounts for obtaining the benefits of each drug, such a delivery system would have a definite use and be a valuable contribution to the dispensing arts. The present invention advances the state of the dispensing art by making available a delivery system housing a number of osmotic delivery devices each having an independent delivery portal for increasing the bioavailability of the drug, the dispersion of drug in a drug receiving environment and concomitantly decreasing the likelihood of local unwanted effects, and for dispensing at least one drug, or at least two different drugs to a biological receptor substantially-free of interaction and drug incompatibility.

OBJECTS OF THE INVENTION

Accordingly, in view of the above presentation it is an immediate object of this invention to provide both a novel and useful drug delivery system that makes a substantial contribution to the art by providing a delivery system useful for obtaining better therapy in the management of health and disease.

Another object of the invention is to provide a delivery system that further perfects drug delivery by having the combined effects of dispersing delivered drug in the biological environment for improving its availability, its absorption and for minimizing local irritation of the biological drug receiving environment.

Another object of the invention is to provide a delivery system for administering a drug in the gastrointestinal tract with a system that is relatively economical in cost to manufacture, provides the clinician with a dependable delivery system, and is well-adapted for practical and acceptable patient use.

Still another object of the invention is to provide a delivery system for administering drug in the gastrointestinal tract by making available a delivery system comprising a multiplicity of miniature osmotic drug delivery devices that diffuse and spread a delivered drug over a larger area of the gastrointestinal tract.

Yet another object of this invention is to provide a delivery system comprising a multiplicity of tiny oral, osmotic drug delivery devices that are simple in construction and exhibit all the practical benefits of controlled and continuous administration of drug during their residency in the stomach and/or the intestine for executing a therapeutic program.

Yet still another object of the invention is to provide a delivery system comprising (1) a plurality of tiny osmotic delivery devices, and (2) a wall surrounding a lumen housing the plurality of osmotic devices, the wall formed of (a) a material that releases the tiny devices into an environment having a pH of 1.0 to 3.5 inclusive, or (b) a material that maintains its physical and chemical integrity in an environment having a pH of 1.0 to 3.5 inclusive, and releases the tiny devices in an environment having a pH of greater than 3.5 to 8.0.

Still another object of this invention to provide an osmotic system that contributes to the dispensing art by making available a system that can dispense at least two different drugs at controlled rates for obtaining the pharmacological and physiological benefit of each drug, and which system thusly represents an improvement and an advancement in the delivery arts.

Another object of the invention is to provide a delivery system housing osmotic devices for separately housing and separately dispensing two drugs essentially-free of chemical interactions attributed to chemical incompatibility, thereby overcoming the problems associated with the prior art.

Another object of the invention is to provide a delivery system that can dispense separately independently continuously at independent controlled rates two or more drugs to a biological drug receptor over a prolonged period of time.

Another object of this invention is to provide a delivery system comprising osmotic devices embracing different structures for dispensing different drugs over time.

Yet still another object of this invention is to provide a delivery system comprising osmotic devices having immediate delivery of drug and delayed delivery of drug for performing a therapeutic program over time.

These objects, as well as other objects, features and advantages of the invention, will become more apparent from the following detailed description of the invention, the drawings, and the accompanying claims.

BRIEF DESCRIPTION OF THE DRAWINGS

In the drawings, which are not drawn to scale, but are set forth to illustrate various embodiments of the invention, the Figures are as follows:

FIGS. 1a and 1b are views partly in section of an opened wall member with an internal space receiving a plurality of miniature osmotic devices from a filling hopper;

FIGS. 2a and 2b are partial, diagrammatic views of filled wall member of FIGS. 1a and 1b being capped for closing the wall member;

FIGS. 3a and 3b illustrate drug delivery systems provided by the invention;

FIG. 4 illustrates the delivery system of FIG. 3a comprising an additional outer wall for regulating the release of drug delivery device from the delivery system;

FIG. 5 depicts an oral osmotic drug delivery device housed in the delivery system; and, FIG. 6 is an opened view of the delivery device of FIG. 5 for illustrating the structure of the delivery device.

In the drawings and the specification, like parts in related Figures are identified by like numbers. The terms appearing earlier in the specification, and in the description of the drawings as well as embodiments thereof, are further described elsewhere in the disclosure.

DETAILED DESCRIPTION OF THE DRAWINGS

Turning now to the drawings in detail, which drawings are an example of the delivery system and the manufacturing procedure provided by the invention, and which examples are not to be construed as limiting, one example of the delivery system and the manufacturing procedure is seen in FIGS. 1 through 6, considered together.

FIGS. 1a and 1b illustrate one manufacturing step in the assembly leading to the delivery system provided by the invention. FIGS. 1a and 1b depict in opened section a body portion 10 comprising a wall 11 surrounding an internal lumen 12. Wall 11 is formed of (a) a material that immediately releases the contents of the delivery system, when the system enters an environment having a pH of 1.0 to 3.5 inclusive, or (b) a material that maintains its physical and chemical integrity in an environment having a pH of 1.0 to 3.5 inclusive, but releases the contents of the delivery system when it enters an environment having a pH of greater than 3.5 to 8.0. Wall 11 surrounds and forms internal lumen 12 and in the embodiment illustrated in FIGS. 1a and 1b it is made as the receiving portion shaped like a capsule. Internal lumen 12 is receiving a multiplicity of tiny osmotic delivery devices 13 from a filling hopper 14. Hopper 14 feeds a predetermined number of tiny osmotic devices 13 into lumen 12.

FIGS. 2a and 2b illustrate another step in the manufacture of the delivery system. In FIGS. 2a and 2b body portion 10 is telescopically capped with an engaging cap portion 15 fed by a capping hopper 16 to yield the delivery system 17 as seen in FIGS. 3a and 3b.

FIG. 4 illustrates delivery system 17 of FIG. 3a comprising an additional outer wall 18. Wall 18 is formed of the delayed release material that keeps its integrity in an environment having a pH of 1.0 to 3.5 inclusive, but released delivery device 13 housed therein when the delivery system passes into an environment having a pH greater than 3.5 to 8.0. Outer wall 18 is an embodiment that can be used when inner wall 11 is made from a material that would release the delivery devices in an environment having a pH of 1.0 to 3.5 inclusive, and it is desired to delay their release until the delivery system enters an environment having a pH of 3.5 to 8.0. Therefore, it will be understood that the inner wall will be made of a material that will lose its physical and chemical integrity at a pH of 1.0 to 8.0.

FIGS. 5 and 6 illustrate osmotic delivery device 13 sized and shaped for housing in delivery system 17. Delivery device 13 of FIG. 5 is seen in opened section in FIG. 6. Delivery device 13 comprises a semipermeable wall 20 that surrounds and defines an internal compartment 21. Semipermeable wall 20 is permeable to the passage of an external fluid present in the environment of use and it is substantially impermeable to the passage of drug and osmotically effective compounds known as osmagents. Compartment 21 contains a drug 22 that is soluble in fluid 23 imbibed into compartment 21 and it exhibits an osmotic pressure gradient across wall 20 against an external fluid. In another embodiment, compartment 21 contains a drug 22 that has limited solubility in fluid that enters compartment 21 and is mixed with an osmotically effective compound that is soluble in fluid 23 imbibed into compartment 21 and exhibits an osmotic pressure gradient across wall 20 against an external fluid. A passageway 24 in semipermeable wall 20 communicates with compartment 21 and the exterior of osmotic device 13 for delivering drug 22 at a controlled and continuous rate over a prolonged period of time. In an embodiment, osmotic device 13 optionally can further comprise an internal partition 25 formed of an expandable material to define expansion compartment 27. Compartment 27 contains osmagent 26 that imbibe fluid 23 into compartment 27 causing compartment 27 to fill with solution, thereby urging partition 25 to expand and assist compartment 21 in dispensing drug 22 through passageway 24 from device 13.

DETAILED DESCRIPTION OF THE INVENTION

In accordance with the practice of this invention, delivery system 17 comprising a wall 11 that surrounds an internal lumen 12 can in one embodiment be made as a capsule. The capsules are made of tasteless materials, they are easily filled and they are easily self-administered by a patient in readily assimilable form. The capsules are conveniently made in two parts, with one part slipping over the other part for completely surrounding delivery device 13 housed therein. The capsules can have a variety of sizes from triple zero to five. The capsules used for the purpose of the invention can be transparent and colorless, or colored capsules can be used to give a special product a distinctive appearance. The capsules can be filled with the drug delivery devices by manual or machine filling methods.

The materials useful for forming wall 11 of delivery system 17 that instantly release delivery device 13 in an environment having a pH of 1.0 to 3.5 inclusive are materials that have a glass transition temperature greater than room temperature, and change their integrity in this environment and concurrently release the delivery devices. The presently preferred materials are pH-sensitive, nontoxic, physiologically inactive, and do not adversely effect the drug and a host. The materials dissolve, disintegrate, degrade, hydrolyze, solublize, are digested, or undergo like change in this biological pH environment. The product produced, as the material changes and releases the tiny osmotic delivery device, is nontoxic, chemically inert, and physiologically inactive. One group of presently preferred materials are polymers, such as proteins having a peptide bond like gelatin of the soft or hard type.

The materials used for forming wall 11 of delivery system 17 that maintains its physical and chemical integrity in an environment having a pH of 1.0 to 3.5 inclusive, and instantly releases delivery device 13 in an environment having a pH of greater than 3.5 to 8.0 are materials such as, (a) polymers having at least one acidic group that enables it to keep its integrity in the lower pH environment, but releases the reservoirs in the higher pH environment, (b) polymers that undergo changes in the higher pH environment by enzymes present in that environment, (c) polymer compositions comprising a polymer and another agent that promote at the higher pH the disintegration of the wall, and the like. Exemplary material that can be used that keep their integrity at a pH of 1.0 to 3.5 inclusive are cellulose carboxylic acid esters, cellulose carboxylic acid ethers, such as cellulose ethyl phthalate, cellulose acetate phthalate, starch acetate phthalate, amylose acetate phthalate, hydroxypropyl methylcellulose phthalate, hydroxypropyl methylcellulose hexahydrophthalate, and the like. Polyacidic acids that keep their integrity at a pH of 1.0 to 3.5 inclusive having acid groups in an undissociated form in this pH range, such as vinyl derivatives of partially hydrolyzed styrene-maleic anhydride copolymer, methylmethacrylate-methacrylic acid copolymer, polymethacrylic acid ester, methylacrylate-methacrylic acid ester, partial alkylene glycol ether esters of $C_1$ to $C_4$ alkyl acrylate unsaturated carboxylic acid anhydride copolymers including maleic, citraconic or itacionic carboxylic acid anhydride, and the like.

Representative of other polymers, and other polymer compositions that comprise at least two ingredients operable for the present purpose of keeping their integrity in a pH range of 1.0 to 3.5 inclusive, are polymers such as shellac, ammoniated shellac, formalized gelatin, polyvinyl acetate phthalate, polyvinyl acetate hyrogenphthalate, and the like; polymer compositions such as a mixture of hydroxyphenyl methylcellulose phthalate and triacetate glycerol in a weight-to-weight ratio of 99-to-1, shellac-formalized gellatin composition, styrene-maleic acid and polyvinyl acetate phthalate composition, shellac and stearic acid composition, and the like.

Semipermeable materials operable for forming wall 20 of delivery device 13 are materials insoluble in body fluids, and they are nonerodible. Typical materials for forming wall 20 include semipermeable polymers such as cellulose acylate, cellulose diacylate, cellulose triacylate, cellulose acetate, cellulose diacetate, cellulose triacetate, and the like. Other semipermeable polymers include polyurethane and selectively permeable polymers including polyurethane, selectively permeable polymers formed by the coprecipitation of a polycation and a polyanion. Generally, semipermeable polymers useful for forming wall 20 will have a fluid permeability of $10^{-5}$ to $10^{-1}$ (cc mil/cm$^2$ hr atm) expressed as per atmosphere of hydrostatic or osmotic pressure difference across wall 20 at the temperature of use. Procedures leading to the manufacture of osmotic devices are described in U.S. Pat. No. 3,845,770 and 3,916,899. Procedures leading to the manufacture of an osmotic device embracing a drug and an expansion compartment separated by a partition are disclosed in U.S. Pat. No. 4,111,202.

The expression passageway 24, as used herein comprises means and methods suitable for releasing drug 22 from compartment 21 to an environment of use. The expresson passageway includes aperture, orifice, bore, or a passageway formed in situ by eroding a water soluble plug, such as a gelatin plug. A detailed description of osmotic passageway, that permits device 13 to function according to osmotic principles and the maximum and the minimum dimensions for a passageway are disclosed in U.S. Pat. Nos. 3,845,770 and 3,916,899. Procedures leading to an osmotically driven active agent dispenser that forms the passageway when the dispenser is in operation are disclosed in U.S. Pat. No. 4,016,880.

The osmotically effective solutes useful in compartment 21 include inorganic and organic compounds that exhibit an osmotic pressure gradient across semipermeable wall 20 against an external fluid. Osmotically effective solutes useful for the present purpose include magnesium sulfate, lactose, urea, inositol, raffinose, sucrose, glucose, lactose, sorbitol and mixtures thereof. Osmotically effective agents and their osmotic pressure in atmospheres are disclosed in U.S. Pat. No. 4,210,139.

In the specification and the accompanying claims, the term drug includes any substance that produces a local or systemic effect, or effects in animals, avians, reptiles and pisces. The term animal includes warm-blooded mammals, primates, humans, household, sport, farm, laboratory and zoo animals. The phrase drug formulation as used herein means drug 22 is in compartment 21 by itself, or drug 22 is in compartment 21 mixed with an osmotic solute, binder or the like. The active drug that can be delivered includes inorganic and organic drugs that act on peripheral nerves, adrenergic receptors, cholinergic receptors, nervous system, skeletal muscles, cardiovascular system, smooth muscles, blood circulatory system, synoptic sites, neuroeffector junctional sites, endocrine and hormone systems, immunological system, reproductive system, skeletal system, autacoid system, tissues, organs, alimentary and excretory systems, inhibitory systems, histamine systems, body passageways, and the like. The drug includes for example, hypnotics, sedatives, psychic energizers, tranqualizers, anti-convulsants, muscle relaxants, antiparkinson, antipyretics, anti-inflammatory, analgesics, anesthetics, hormones, anti-microbials, sympathomimetics, diuretics, neoplastics, hypoglycemics, amino acids, opthalmics, vitamins, and the like. The delivery system in one embodiment can house osmotic delivery device containing the same drug, and in another embodiment the delivery system can house osmotic delivery devices containing like and unlike drugs. The inventive advantage provided by the osmotic devices each containing different drugs is that interaction among drugs that adversely effect each other is avoided, leading to better stability of delivered drug, and drug is delivered in the gastrointestinal tract substantially free of irritating the gastrointestinal mucus tissues. Also, drugs that have different rates of hydrolysis, different rates of oxidation, different rates of decomposition, different rates of delivery and different rates of bioneed can now be made into dosage form and dispensed essentials free of one drug influence or effecting another drug. The delivery system can house in the internal space both delivery devices and drug, which latter drug is available for instant use by a host, or the semipermeable wall of the osmotic device can carry an enteric coating for delayed release of drug. The present invention provides a delivery system for administering drug, by making available a delivery system comprising osmotic devices representing a plurality of preformed passageways for dispensing and dispersing drug, and for enhancing its availability for use in better therapy. The beneficial drugs, and the amount to be delivered are known to the dispensing art in *Pharmaceutical Sciences*, by Remington, 14th Ed., 1970, published by Mack Publishing Co., Easton, PA; and in *The Pharmacological Basis of Therapeutics*, by Goodman and Gilman, 4th Ed., 1970 published by the MacMillian Co., London.

Drug 22 can be present in compartment 21 in various forms, such as uncharged molecules, molecular complexes, as therapeutically acceptable addition salts, such as hydrochlorides, hydrobromides, sulfates, oleates and the like. For acid drugs, salts of metals, amines, organic cations, quaternary ammonium salts can be used. Derivatives of drugs such as esters, ethers and amides can be used. A drug that is water insoluble can be use in a form that is water soluble derivative thereof to serve as a solute, and on its release from the delivery system is converted by enzymes, hydrolyzed by body pH, or other metabolic processes to the original biologically active form. The amount of drug in compartment 21 of a tiny osmotic delivery device 13 generally is about 10 ng to 50 mg. The number of tiny osmotic devices in a delivery system is at least two or more, more preferably about 5 to 750, and still more preferrably about 5 to 100.

The drug delivery device 13 used for the purpose of the invention, is manufactured by standard techniques. For example, in one embodiment drug and a binder are mixed into a solid, semi-solid, or pressed into a miniature shaped form by conventional methods. Then, a wall forming material is applied by molding, spraying or dipping the pressed drug shape into the wall forming material. In another embodiment, a wall can be cast, shaped to the desired dimensions that surround compartment 21, the compartment filled with drug, closed and a passageway drilled through the wall. For osmotic devices manufactured smaller than 2 mm in diameter, the passageway is preferrably made by the in situ method described in U.S. Pat. No. 4,016,880. In a presently preferred embodiment the delivery device is made by using an air suspension technique. This process consists in compressing a drug, and then suspending and tumbling the drug in a wall forming composition until the wall is applied around the drug. Next, after drying, a passageway is drilled in the wall. The air suspension procedure is described in U.S. Pat. No. 2,799,241; in *J. Am. Pharm. Assoc.*, Vol. 48, pages 451 to 459, 1959; and ibid., Vol. 49, pages 82 to 84, 1960. Other wall forming techniques such as pan coating can be used in which materials are deposited by successive spraying of the polymer solution on the drug, or solute, accompanied by tumbling in a rotating pan. Generally, a semipermeable wall will be about 0.5 to 10 mils thick. Of course, thinner and thicker walls are within the scope of the invention.

Delivery system 17 comprising body member 10 can be made by procedures such as dipping a mold element, having a shape corresponding to the shape illustrated in FIG. 1a, or 1b, for example, into a bath of a wall 11 forming material, such as a solution of aqueous gelatin. The mold element is submerged within the aqueous gelatin to form the desired coat on the mold element. Next, the coated mold is pulled from the solution, allowed to cool, and then stripped from the mold to yield the wall member with an internal lumen. The wall can be made from enteric material by dissolving for example hydroxypropyl methylcellulose phthalate in an aqueous solution of an alkali base to obtain an aqueous solution corresponding to the alkali metal salt of hydroxypropyl methylcellulose phthalate. Typical alkali bases are sodium carbonate, potassium carbonate, sodium hydroxide, and the like. Next, an aqueous gelatin solution is added to the solution of the alkali metal salt of hydroxypropyl methylcellulose phthalate, and molds are immersed into the solution, withdrawn and the materials on the molds cooled at room temperature, or lower. Next, the capsule portion is removed from the mold. Manufacturing procedures for making capsules are disclosed in U.S. Pat. Nos. 1,527,659; 2,299,039; and 3,826,666.

Exemplary solvents suitable for manufacturing semipermeable wall 20 are inert inorganic and organic solvents that do not adversely harm the wall forming materials, the drug and the final osmotic device. The solvents broadly include aqueous solvents, alcohols, ketones, esters, ethers, aliphatic hydrocarbons, halogenated solvents, cycloaliphatic aromatics, heterocyclic solvents and the like. Typical solvents include acetone, methanol, ethanol, isopropyl alcohol, methyl acetate, ethyl acetate, methyl isobutyl ketone, n-hexane, methylene chloride, ethylene dichloride, mixtures such as acetone and water, acetone and methanol, acetone and ethyl alcohol, methylene dichloride and methanol, ethylene dichloride and methanol, and mixtures thereof.

DESCRIPTION OF EXAMPLES

The following examples will serve to further illustrate the present invention, and they should not be considered as limiting the scope of the invention in any way, as these examples and other equivalents thereof will become apparent to those versed in the art in the light of the present disclosure, drawings, and the accompanying claims.

EXAMPLE 1

First, 100 mg of procainamide hydrochloride and 5 mg of binder polyvinyl pyrrolidone are blended into a homogenous composition and passed through a 20 mesh screen to form a number of precores of drug. The precores next are compressed into round cores about 5 mm in diameter and then transferred to an air suspension machine. The compressed drug cores contain about 20 mg of drug and are coated with cellulose acetate having an acetyl content of 32% using a 5% polymer solution in dioxane to produce tiny osmotic drug delivery devices haviang a semipermeable wall about 6 mils thick. After the delivery devices are dried for 10 days at about 55° C., an osmotic passageway about 4 mils in diameter is laser drilled through the semipermeable wall. Finally, a number of receiving capsules are filled with 5 osmotic devices and capped with the closing portion of the capsule to yield the delivery system. The wall of the delivery system comprises polymeric gelatinthat releases the delivery devices in an environment having a pH of 1.0 to 3.5 inclusive.

EXAMPLE 2

A delivery device is made by first preparing drug reservoirs comprising potassium chloride by blending 1 kg of potassium chloride and 3 ml of a 20% solution of acacia to form a homogeneous blend. Next, the blend is passed through an extrusion granulation machine, dried at 115°–120° F. for 12 hours and the reservoir forming cores passed through a 20 mesh screen. The cores are coated next in an air suspension machine with a 5% solution of cellulose acetate in a methylene chloride-methanol solvent, 89:11, wt:wt, with a semipermeable wall 7 mils thick. The coated drug is dried at 55° C. for 48 hours in an air oven, and then osmotic passageways are laser drilled in each device. The passageway had a diameter of about $42 \times 10^{-1}$ mils.

The tiny osmotic delivery devices are transferred to a feeding hopper and 15 devices are fed into the receiving portion of a capsule, and then the filled portion is moved to the next position in the filling line where the receiving portion is telescopically capped with an engaging cap portion to produce the completed delivery system. The receiving and cap portions are made from a wall forming composition comprising cellulose acetate phthalate and formalized gelatin, which composition keeps its integrity at a pH of 1.0 to 3.5 inclusive, and releases the tiny osmotic devices at a pH of greater than 3.5 to 8.0.

EXAMPLE 3

Drug delivery devices are prepared according to the procedures of the above examples. The drug reservoirs for this example are made from 375 g of aminophylline, 15.5 g of mannitol, and 1.5 g of magnesium stearate, and formulated into tiny compressed drug cores. The cores are coated with a semipermeable wall of cellulose acetate having an acetyl content of 38.3%, and a passageway laser drilled therethrough. Then, 15 of the tiny drug delivery devices are surrounded by a wall having first or inner lamina of gelatin, and then a second, or outer lamina of hydroxypropyl methylcellulose phthalate is laminated onto the inner lamina by dipping the delivery system with a bath containing hydroxypropyl methylcellulose.

EXAMPLE 4

The drug delivery systems prepared according to Example 1 are placed in an air suspension machine, and a volatile coating composition comprising an acrylic based resin in isopropyl alcohol is injected through a port into the machine for applying a coat onto the delivery system.

EXAMPLE 5

An osmotic delivery device for the controlled and continuous delivery of the beneficial drug hydralazine hydrochloride to a biological environment of use is made as follows: first a compartment forming composition is compounded from 50 mg of hydralazine hydrochloride, 208.5 mg of mannitol, 8 mg of hydroxypropyl methylcellulose and 8 mg of stearic acid by mixing the hydralazine hydrochloride and the mannitol and then passing the mixture through a 40-mesh screen; next, the hydroxypropyl methylcellulose is dissolved in 70/30 (w/w%) ethanol-water solution and the hydralazine mannitol mixture added to the wet hydroxypropyl methylcellulose and all the ingredients blended for 10 minutes. Next, the blend is passed through a 10-mesh screen and spread on a tray and dried in a forced air oven at 50° C. for 18–24 hours. The dried blend is passed through a 20-mesh screen, placed in a mixer, and the stearic acid added to the blend and the mixing continued for 10 minutes. Then, 35 mm of the hydralazine drug formulation reservoir is pressed under a pressure head into a 4 mm core and then coated in an air suspension machine with a wall of semipermeable cellulose acetate composition comprising 40% cellulose acetate having an acetyl content of 32%, 42% cellulose acetate having an acetyl content of 39.8%, and 18% hydroxypropyl methylcellulose, coated from an 80 to 20 parts by weight solvent of methylene chloride-methanol solvent. The coated osmotic device is dried in a forced air oven at 50° C. for one week, and then a laser passageway is drilled through the semipermeable wall.

A different reservoir forming composition comprising 19 mg of metoprolol fumurate, 1.4 mg of sodium bicarbonate, 1.6 mg of polyvinyl pyrrolidone and 0.32 mg of magnesium stearate is made by first mixing the metoprolol fumarate with sodium bicarbonate and passing the mixture through a 40-mesh screen, then, the polyvinyl pyrrolidone is mixed with 2 ml of an ethanol and 1 ml of water solution, and the freshly prepared polyvinyl pyrrolidone solution is added slowly with mixing to the metoprolol fumarate sodium bicarbonate mixture. The ingredients are mixed for 20 minutes, passed through a 10-mesh screen and dried in a forced air oven for 24 hours. Next, the dried blend is passed through a 20-mesh screen, placed in a mixer, the magnesium stearate added and the ingredients again blended to yield the reservoir composition. Then, the metoprolol fumarate drug formulation is compressed into a solid core and coated in an air suspension machine with a wall of semipermeable cellulose acetate composition comprising 40% cellulose acetate having an acetyl content of 32%, 42% cellulose acetate having an acetyl content of 39.8%, and 18% hydroxypropyl methylcellulose, from an 80 to 20 parts by weight solvent of methylene chloride-methanol solvent. The coated osmotic device is dried in a forced air oven at 50° C. for one week, and then a laser passageway is drilled through the semipermeable wall. Finally a plurality of the osmotic devices containing the hydralazine and a plurality of the osmotic devices containing the metoprolol are charged into the lumen of a housing to yield the delivery system. The osmotic devices orn their release from the housing in a gastrointestinal tract deliver the drugs with dispersion throughout the tract substantially free of tissue irritation.

It will be appreciated by those versed in the drug dispensing art that the present invention advances the state-of-the-art by providing (a) a delivery system that can provide in vivo a multiplicityr of tiny osmotic drug delivery devices that can deliver drug-in-solution as the devices travel through the biological environment; (b) a delivery system that can provide tiny osmotic devices for minimizing gastrointestinal irritation; (c) a delivery system that can provide tiny osmotic devices for continuous and steady release for producing constant and steady absorption of delivered drug; and (d) provide a delivery system that can deliver drug from a plurality of tiny osmotic device in solution in the stomach and/or the intestine over time. Also it will be understood by those knowledgeable in the delivery art that many embodiments of this invention can be made without departing from the spirit and scope of the invention, and the invention is not to be construed as limiting, as it embraces all equivalents thereof.

We claim:

1. A delivery system for delivering a beneficial agent formulation, the delivery system comprising:
   (a) a wall that surrounds and forms an internal space, the wall comprising an inner lamina comprising a pH sensitive material that loses its physical and chemical integrity at a pH of 1.0 to 8.0 inclusive, and an outer lamina comprising a pH sensitive material that maintains its physical and chemical integrity at a pH of 1.0 and 3.5 inclusive, and loses its physical and chemical integrity at a pH of 3.5 to 8.0;
   (b) a plurality of tiny osmotic delivery devices useful for delivering a beneficial agent formulation and for co-delivering beneficial agent formulation combinations having a different biological half-life and therapeutic index in the space, the osmotic delivery devices comprising:
   (1) a semipermeable wall that surrounds and forms an internal compartment in the osmotic delivery device, the wall comprising a material that is permeable to the passage of an external fluid and substantially impermeable to the passage of a beneficial agent formulation;
   (2) a beneficial agent formulation in the compartment of each tiny osmotic delivery device that is soluble in fluid imbibed into the compartment and exhibits an osmotic pressure gradient across the semipermeable wall of the osmotic delivery device against an external fluid; and,
   (3) an osmotic passageway in the semipermeable wall of each tiny osmotic delivery device that communicates with the compartment containing the beneficial agent formulation and the exterior of the osmotic device for delivering the beneficial agent formulation through the passageway from the tiny osmotic device over time.

2. A delivery system for delivering a beneficial agent formulation, the delivery system comprising:
   (a) a wall surrounding an internal lumen, said wall comprising a material that substantially maintains its physical and chemical integrity at a pH of 1.0 to 3.5 inclusive and loses its physical and chemical integrity at a pH of 3.5 to 8.0; and
   (b) a multiplicity of tiny osmotic delivery devices useful for delivering a beneficial agent formulation and for co-delivering beneficial agent formulation combinations having a different biological half-life and therapeutic index in the lumen, said osmotic deliveryr devices comprising:
   (1) a wall surrounding and forming an internal compartment, said wall comprising a material that is permeable to the passage of an external fluid and substantially impermeable to the passage of a beneficial agent formulation;
   (2) a beneficial agent formulation in the compartment of each osmotic delivery device that is soluble in fluid imbibed into the compartment and exhibits an osmotic pressure gradient across the wall of the osmotic delivery device against an external fluid; and,
   (3) an independent osmotic passageway in the wall of each osmotic delivery device that permits the osmotic delivery device to function according to osmotic principles, which osmotic passageway communicates with the compartment containing the beneficial agent formulation and the exterior of the osmotic delivery device for delivering the beneficial agent formulation from the tiny osmotic device.

* * * * *